(12) United States Patent
Inman

(10) Patent No.: US 7,974,707 B2
(45) Date of Patent: Jul. 5, 2011

(54) ELECTRODE ASSEMBLY WITH FIBERS FOR A MEDICAL DEVICE

(75) Inventor: D. Michael Inman, Gainesville, FL (US)

(73) Assignee: Cyberonics, Inc., Houston, TX (US)

( * ) Notice: Subject to any disclaimer, the term of this patent is extended or adjusted under 35 U.S.C. 154(b) by 819 days.

(21) Appl. No.: 11/627,872

(22) Filed: Jan. 26, 2007

(65) Prior Publication Data

US 2008/0183258 A1    Jul. 31, 2008

(51) Int. Cl.
*A61N 1/05* (2006.01)
(52) U.S. Cl. .................................................... 607/118
(58) Field of Classification Search .................. None
See application file for complete search history.

(56) References Cited

U.S. PATENT DOCUMENTS

| | | | |
|---|---|---|---|
| 3,421,511 A | 1/1969 | Schwartz et al. | |
| 3,760,812 A | 9/1973 | Timm et al. | |
| 3,796,221 A | 3/1974 | Hagfors | |
| 4,291,699 A | 9/1981 | Geddes et al. | |
| 4,305,402 A | 12/1981 | Katims | |
| 4,384,926 A | 5/1983 | Wagner | |
| 4,407,303 A * | 10/1983 | Akerstrom | 607/126 |
| 4,458,696 A | 7/1984 | Larimore | |
| 4,459,989 A | 7/1984 | Borkan | |
| 4,573,481 A | 3/1986 | Bullara | |
| 4,590,946 A | 5/1986 | Loeb | |
| 4,592,359 A | 6/1986 | Galbraith | |
| 4,606,349 A | 8/1986 | Livingston et al. | |
| 4,608,985 A | 9/1986 | Crish et al. | |
| 4,612,934 A | 9/1986 | Borkan | |
| 4,628,942 A | 12/1986 | Sweeney et al. | |
| 4,630,615 A | 12/1986 | Yomtov | |
| 4,649,936 A | 3/1987 | Ungar et al. | |
| 4,702,254 A | 10/1987 | Zabara | |
| 4,793,353 A | 12/1988 | Borkan | |
| 4,821,724 A | 4/1989 | Whigham et al. | |
| 4,827,932 A | 5/1989 | Ideker et al. | |
| 4,850,356 A | 7/1989 | Heath | |

(Continued)

FOREIGN PATENT DOCUMENTS

WO    2004/069330    8/2004

OTHER PUBLICATIONS

J. Walter Woodbury and Dixon M. Woodbury, Vagal Stimulation Reduces the Severity of Maximal Electroshock Seizures in Intact Rates: Use of a Cuff Electrode for Stimulating and Recording, Department of Physiology, School of Medicine, University of Utah, Jan. 1991, pp. 94-107, vol. 14, Salt Lake City, Utah.

(Continued)

*Primary Examiner* — Carl H Layno
*Assistant Examiner* — Paula J Stice
(74) *Attorney, Agent, or Firm* — Toler Law Group; Jonathan D. Rowell; Darrell N. Fuller

(57) ABSTRACT

An apparatus and system are provided for employing an electrode for delivering an electrical signal to a portion of a tissue of a patient's body. The electrode includes a first surface to electrically couple to the portion of an outer layer of the tissue. The electrode also includes a plurality of fibers or longitudinal elements coupled to the outer surface. The plurality of fibers or longitudinal elements are adapted to migrate to an interior portion of the tissue.

18 Claims, 9 Drawing Sheets

U.S. PATENT DOCUMENTS

| | | |
|---|---|---|
| 4,860,616 A | 8/1989 | Smith |
| 4,867,164 A | 9/1989 | Zabara |
| 4,870,341 A | 9/1989 | Pihl et al. |
| 4,899,750 A | 2/1990 | Ekwall |
| 4,903,700 A | 2/1990 | Whigham et al. |
| 4,920,979 A | 5/1990 | Bullara |
| 4,964,407 A | 10/1990 | Baker, Jr. et al. |
| 4,969,468 A * | 11/1990 | Byers et al. ............ 600/373 |
| 4,979,511 A | 12/1990 | Terry, Jr. |
| 5,003,975 A | 4/1991 | Hafelfinger et al. |
| 5,025,807 A | 6/1991 | Zabara |
| 5,095,905 A | 3/1992 | Klepinski |
| 5,111,815 A | 5/1992 | Mower |
| 5,137,020 A | 8/1992 | Wayne et al. |
| 5,137,021 A | 8/1992 | Wayne et al. |
| 5,139,028 A | 8/1992 | Steinhaus et al. |
| 5,146,920 A | 9/1992 | Yuuchi et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,201,808 A | 4/1993 | Steinhaus et al. |
| 5,201,865 A | 4/1993 | Kuehn |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,515 A | 7/1994 | Rutecki et al. |
| 5,335,657 A | 8/1994 | Terry, Jr. et al. |
| 5,351,394 A | 10/1994 | Weinberg |
| 5,411,528 A | 5/1995 | Miller et al. |
| 5,431,692 A | 7/1995 | Hansen et al. |
| 5,466,255 A * | 11/1995 | Franchi .................. 607/128 |
| 5,501,702 A | 3/1996 | Plicchi et al. |
| 5,507,786 A | 4/1996 | Morgan et al. |
| 5,522,865 A | 6/1996 | Schulman et al. |
| 5,531,778 A | 7/1996 | Maschino et al. |
| 5,534,018 A | 7/1996 | Wahlstrand et al. |
| 5,540,730 A | 7/1996 | Terry, Jr. et al. |
| 5,540,734 A | 7/1996 | Zabara |
| 5,549,646 A | 8/1996 | Katz et al. |
| 5,571,150 A | 11/1996 | Wernicke et al. |
| 5,575,813 A | 11/1996 | Edell et al. |
| 5,620,474 A | 4/1997 | Koopman |
| 5,658,318 A | 8/1997 | Stroetmann et al. |
| 5,690,681 A | 11/1997 | Geddes et al. |
| 5,700,282 A | 12/1997 | Zabara |
| 5,707,400 A | 1/1998 | Terry, Jr. et al. |
| 5,713,936 A | 2/1998 | Staub et al. |
| 5,741,311 A | 4/1998 | Mc Venes et al. |
| 5,743,860 A | 4/1998 | Hively et al. |
| 5,755,742 A | 5/1998 | Schuelke et al. |
| 5,755,747 A | 5/1998 | Daly et al. |
| 5,759,199 A | 6/1998 | Snell et al. |
| 5,769,873 A | 6/1998 | Zadeh |
| 5,796,044 A | 8/1998 | Cobian et al. |
| 5,814,088 A | 9/1998 | Paul et al. |
| 5,876,425 A | 3/1999 | Gord et al. |
| 5,891,179 A | 4/1999 | Er et al. |
| 5,897,577 A | 4/1999 | Cinbis et al. |
| 5,916,239 A | 6/1999 | Geddes et al. |
| 5,919,220 A * | 7/1999 | Stieglitz et al. ............ 607/118 |
| 5,928,272 A | 7/1999 | Adkins et al. |
| 5,995,868 A | 11/1999 | Dorfmeister et al. |
| 6,035,237 A | 3/2000 | Schulman et al. |
| 6,052,624 A | 4/2000 | Mann |
| 6,073,050 A | 6/2000 | Griffith |
| 6,104,956 A | 8/2000 | Naritoku et al. |
| 6,154,678 A | 11/2000 | Lauro |
| 6,171,239 B1 * | 1/2001 | Humphrey ............ 600/372 |
| 6,181,969 B1 | 1/2001 | Gord |
| 6,208,902 B1 | 3/2001 | Boveja |
| 6,212,431 B1 | 4/2001 | Hahn et al. |
| 6,216,045 B1 | 4/2001 | Black et al. |
| 6,259,951 B1 | 7/2001 | Kuzma et al. |
| 6,269,270 B1 | 7/2001 | Boveja |
| 6,304,787 B1 | 10/2001 | Kuzma et al. |
| 6,317,633 B1 | 11/2001 | Jorgenson et al. |
| 6,339,725 B1 | 1/2002 | Naritoku et al. |
| 6,341,236 B1 | 1/2002 | Osorio et al. |
| 6,393,325 B1 | 5/2002 | Mann et al. |
| 6,400,988 B1 | 6/2002 | Gurewitsch |
| 6,418,348 B1 | 7/2002 | Witte |
| 6,445,951 B1 | 9/2002 | Mouchawar |
| 6,453,198 B1 | 9/2002 | Torgerson et al. |
| 6,456,481 B1 | 9/2002 | Stevenson |
| 6,473,653 B1 | 10/2002 | Schallhorn et al. |
| 6,477,417 B1 | 11/2002 | Levine |
| 6,490,486 B1 | 12/2002 | Bradley |
| 6,505,074 B2 | 1/2003 | Boveja et al. |
| 6,510,332 B1 | 1/2003 | Greenstein |
| 6,529,774 B1 | 3/2003 | Greene |
| 6,553,263 B1 | 4/2003 | Meadows et al. |
| 6,556,868 B2 | 4/2003 | Naritoku et al. |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,600,957 B2 | 7/2003 | Gadsby |
| 6,606,523 B1 | 8/2003 | Jenkins |
| 6,609,025 B2 | 8/2003 | Barrett et al. |
| 6,620,186 B2 | 9/2003 | Saphon et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,648,823 B2 | 11/2003 | Thompson |
| 6,658,294 B1 | 12/2003 | Zadeh et al. |
| 6,662,053 B2 | 12/2003 | Borkan |
| 6,671,556 B2 | 12/2003 | Osorio et al. |
| 6,684,105 B2 | 1/2004 | Cohen et al. |
| 6,687,538 B1 | 2/2004 | Hrdlicka et al. |
| 6,690,974 B2 | 2/2004 | Archer et al. |
| 6,711,440 B2 | 3/2004 | Deal et al. |
| 6,718,203 B2 | 4/2004 | Weiner et al. |
| 6,718,207 B2 | 4/2004 | Connelly |
| 6,721,600 B2 | 4/2004 | Jorgenson et al. |
| 6,721,603 B2 | 4/2004 | Zabara et al. |
| 6,725,092 B2 | 4/2004 | MacDonald et al. |
| 6,731,979 B2 | 5/2004 | MacDonald |
| 6,745,077 B1 | 6/2004 | Griffith et al. |
| 6,754,539 B1 | 6/2004 | Erickson et al. |
| 6,757,566 B2 | 6/2004 | Weiner et al. |
| 6,760,624 B2 | 7/2004 | Anderson et al. |
| 6,760,625 B1 | 7/2004 | Kroll |
| 6,760,628 B2 | 7/2004 | Weiner et al. |
| 6,763,268 B2 | 7/2004 | MacDonald et al. |
| 6,778,856 B2 | 8/2004 | Connelly et al. |
| 6,792,316 B2 | 9/2004 | Sass |
| 6,795,730 B2 | 9/2004 | Connelly et al. |
| 6,795,736 B2 | 9/2004 | Connelly et al. |
| 6,799,069 B2 | 9/2004 | Weiner et al. |
| 6,804,557 B1 | 10/2004 | Kroll |
| 6,819,954 B2 | 11/2004 | Connelly |
| 6,819,958 B2 | 11/2004 | Weiner et al. |
| 6,829,509 B1 | 12/2004 | MacDonald et al. |
| 6,843,870 B1 | 1/2005 | Bluger |
| 6,845,266 B2 | 1/2005 | Weiner et al. |
| 6,850,805 B2 | 2/2005 | Connelly et al. |
| 6,875,180 B2 | 4/2005 | Weiner et al. |
| 6,901,290 B2 | 5/2005 | Foster et al. |
| 6,906,256 B1 | 6/2005 | Wang |
| 6,907,295 B2 | 6/2005 | Gross et al. |
| 6,920,357 B2 | 7/2005 | Osorio et al. |
| 6,925,328 B2 | 8/2005 | Foster et al. |
| 6,944,489 B2 | 9/2005 | Zeijlemaker et al. |
| 6,949,929 B2 | 9/2005 | Gray et al. |
| 6,954,674 B2 | 10/2005 | Connelly |
| 6,961,618 B2 | 11/2005 | Osorio et al. |
| 6,985,775 B2 | 1/2006 | Reinke et al. |
| 6,993,387 B2 | 1/2006 | Connelly et al. |
| 7,006,859 B1 | 2/2006 | Osorio et al. |
| 7,010,357 B2 | 3/2006 | Helfer et al. |

| | | |
|---|---|---|
| 7,013,174 B2 | 3/2006 | Connelly et al. |
| 7,015,393 B2 | 3/2006 | Weiner et al. |
| 7,047,074 B2 | 5/2006 | Connelly et al. |
| 7,054,686 B2 | 5/2006 | MacDonald |
| 7,107,097 B2 | 9/2006 | Stern et al. |
| 7,123,013 B2 | 10/2006 | Gray |
| 7,171,166 B2 | 1/2007 | Ng et al. |
| 7,174,219 B2 | 2/2007 | Wahlstrand et al. |
| 7,212,869 B2 * | 5/2007 | Wahlstrom ............... 607/126 |
| 7,221,981 B2 | 5/2007 | Gliner |
| 7,239,924 B2 * | 7/2007 | Kolberg ............... 607/126 |
| 7,289,856 B1 | 10/2007 | Karicherla |
| 7,584,004 B2 * | 9/2009 | Caparso et al. ............. 607/118 |
| 2002/0072782 A1 | 6/2002 | Osorio et al. |
| 2003/0083726 A1 | 5/2003 | Zeijlemaker et al. |
| 2003/0195601 A1 | 10/2003 | Hung et al. |
| 2004/0015205 A1 | 1/2004 | Whitehurst et al. |
| 2004/0147992 A1 | 7/2004 | Bluger et al. |
| 2004/0167583 A1 | 8/2004 | Knudson et al. |
| 2004/0172088 A1 | 9/2004 | Knudson et al. |
| 2004/0210291 A1 | 10/2004 | Erickson |
| 2005/0015128 A1 | 1/2005 | Rezai et al. |
| 2005/0016657 A1 | 1/2005 | Bluger |
| 2005/0107858 A1 | 5/2005 | Bluger |
| 2005/0154426 A1 | 7/2005 | Boveja et al. |
| 2005/0154435 A1 | 7/2005 | Stern et al. |
| 2005/0222642 A1 | 10/2005 | Przybyszewski et al. |
| 2005/0272280 A1 | 12/2005 | Osypka |
| 2006/0058597 A1 | 3/2006 | Machado et al. |
| 2006/0106430 A1 | 5/2006 | Fowler et al. |
| 2006/0167497 A1 | 7/2006 | Armstrong et al. |
| 2006/0173493 A1 | 8/2006 | Armstrong et al. |
| 2006/0184211 A1 | 8/2006 | Gaunt et al. |
| 2006/0224199 A1 | 10/2006 | Zeijlemaker et al. |
| 2006/0253164 A1 | 11/2006 | Zhang et al. |
| 2006/0265025 A1 | 11/2006 | Goetz et al. |
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0060991 A1 | 3/2007 | North et al. |
| 2007/0073150 A1 | 3/2007 | Gopalsami et al. |
| 2007/0100392 A1 | 5/2007 | Maschino et al. |
| 2007/0142889 A1 * | 6/2007 | Whitehurst et al. .......... 607/118 |
| 2007/0173902 A1 | 7/2007 | Maschino et al. |
| 2007/0179557 A1 | 8/2007 | Maschino et al. |
| 2007/0179579 A1 | 8/2007 | Feler et al. |
| 2007/0179584 A1 | 8/2007 | Gliner |
| 2008/0033503 A1 | 2/2008 | Fowler et al. |
| 2008/0046035 A1 | 2/2008 | Fowler et al. |
| 2008/0071323 A1 | 3/2008 | Lowry et al. |
| 2008/0200925 A1 | 8/2008 | Johnson et al. |
| 2008/0215110 A1 | 9/2008 | Gunderson et al. |
| 2008/0255582 A1 | 10/2008 | Harris |
| 2009/0076567 A1 | 3/2009 | Fowler et al. |

OTHER PUBLICATIONS

Mesut Sahin, Improved Nerve Cuff Electrode Recordings with Sub-threshold Anodic Currents, IEEE Transactions on Biomedical Engineering, Aug. 1998, pp. 1044-1050, vol. 45, No. 8.

Peter J. Basser and Bradley J. Roth, New Currents in Electrical Stimulation of Excitable Tissues, Annu. Rev. Biomed. Eng. 2000, vol. 2, pp. 377-397.

* cited by examiner

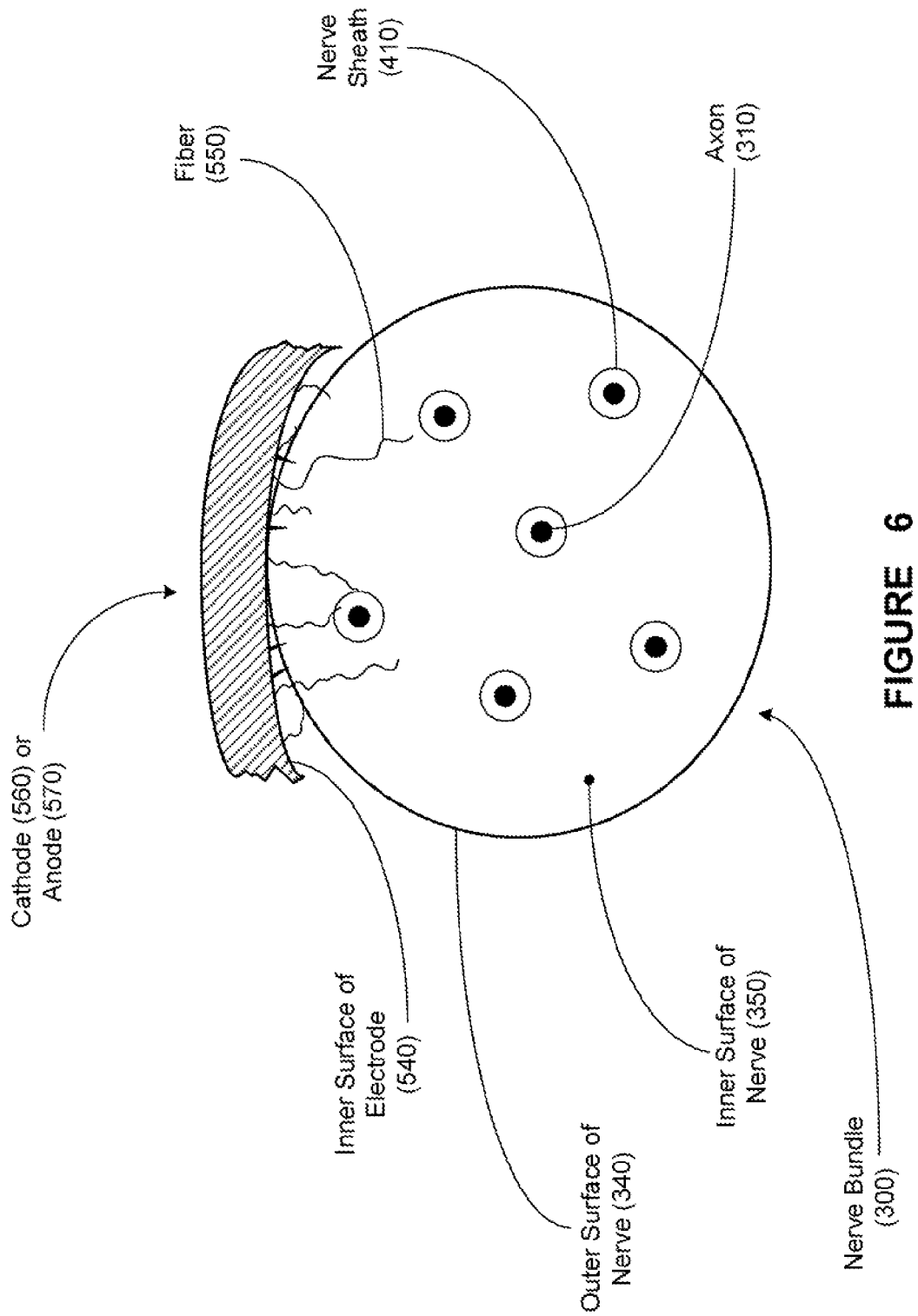

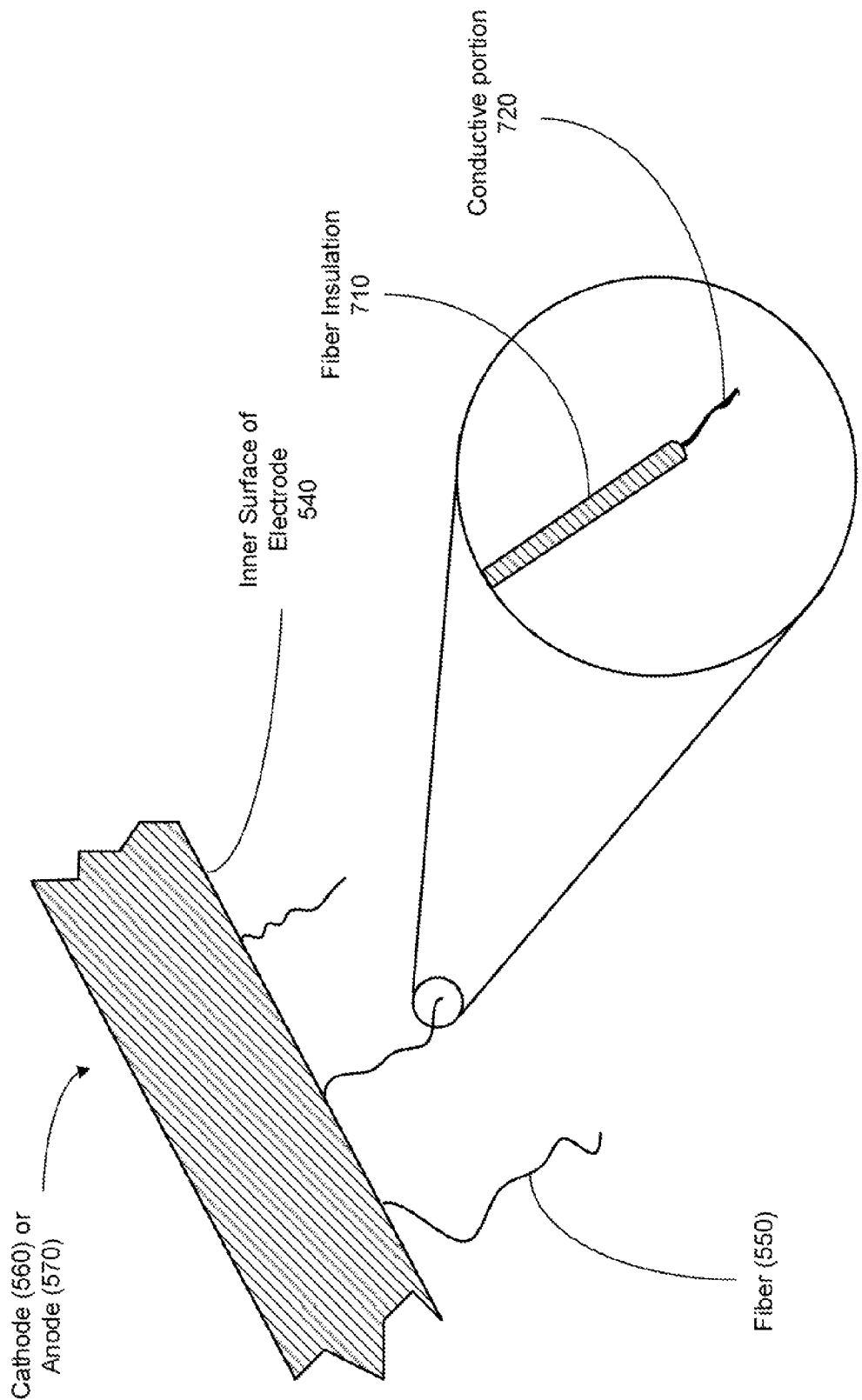

ELECTRODE ASSEMBLY WITH FIBERS FOR A MEDICAL DEVICE

BACKGROUND OF THE INVENTION

1. Field of the Invention

This invention relates generally to an apparatus for delivering an electrical signal to a patient's body using an implantable medical device (IMD) system and, more particularly, an electrode comprising fibrous components for improved electrical contact with a targeted portion of the patient's body for delivering a stimulation signal from an IMD.

2. Description of the Related Art

Many advancements have been made in treating diseases such as epilepsy. Therapies using electrical signals for treating these diseases have been found to be effective. IMDs have been effectively used to deliver therapeutic stimulation to various portions of the human body (e.g., the vagus nerve) for treating these diseases. As used herein, "stimulation" or "stimulation signal" refers to the application of an electrical, mechanical, magnetic, electro-magnetic, photonic, audio and/or chemical signal to a target tissue in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio, or chemical in nature) applied to the tissue in the present invention is a signal applied from an artificial source, e.g., a neurostimulator.

A "therapeutic signal" refers to a stimulation signal delivered to a patient's body with the intent of treating a disorder by providing a modulating effect to the target tissue, e.g., a neural tissue. The effect of a stimulation signal on electrical, chemical and/or mechanical activity in the target tissue is termed "modulation"; however, for simplicity, the terms "stimulating" and "modulating", and variants thereof, are sometimes used interchangeably herein. In general, however, the delivery of an exogenous signal itself refers to "stimulation" of the target tissue, while the effects of that signal, if any, on the electrical, chemical and/or mechanical activity of the target tissue are properly referred to as "modulation." The modulating effect of the stimulation signal upon the target tissue may be excitatory or inhibitory, and may potentiate acute and/or long-term changes in electrical, chemical and/or mechanical activity. For example, the "modulating" effect of the stimulation signal to a target neural tissue may comprise one more of the following effects: (a) initiation of an action potential (afferent and/or efferent action potentials); (b) inhibition or blocking of the conduction of action potentials, whether endogenously or exogenously induced, including hyperpolarizing and/or collision blocking, (c) affecting changes in neurotransmitter/neuromodulator release or uptake, and (d) changes in neuro-plasticity or neurogenesis of brain tissue.

Electrical neurostimulation may be provided by implanting an electrical device underneath the patient's skin and delivering an electrical signal to a nerve, such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may apply a series of electrical pulses to the nerve (e.g., a cranial nerve such as a vagus nerve) periodically, intermittently, or continuously throughout the day, or over another predetermined time interval. This type of stimulation is generally referred to as "passive," "non-feedback," or "prophylactic," stimulation. The electrical signal may be applied by an IMD that is implanted within the patient's body. In another alternative embodiment, the signal may be generated by an external pulse generator outside the patient's body, coupled by an RF or wireless link to an implanted electrode.

Generally, neurostimulation signals that perform neuromodulation are delivered by the IMD via one or more leads. The leads generally terminate at their distal ends in one or more electrodes, and the electrodes, in turn, are electrically coupled to tissue in the patient's body. For example, a number of electrodes may be attached to various points of a nerve or other tissue inside a human body for delivery of a neurostimulation signal.

Turning now to FIG. 1, a prior art electrode assembly 100 operatively coupled to a nerve bundle 120 comprising a plurality of individual nerve fibers or axons, is illustrated. The electrode assembly 100 comes into contact with the external periphery of the nerve 120 to deliver an electrical signal to the nerve. The electrode assembly 100 includes a first helical portion 112, a second helical portion 114 and an anchor 116 that couples the electrode to the nerve bundle 120. The first helical portion 112 may be a cathode portion, and the second helical portion 114 may be an anode portion of the electrode assembly 100. The electrode assembly 100 is coupled to a lead that carries an electrical signal from the IMD Typically, state-of-the-art neurostimulation electrodes deliver electrical signals to the outer surface 140 of nerve bundle 120. Generally, this disposition of the stimulation electrode assembly 100 only provides penetration of electrical charge into areas near the outer surface 140 of the nerve bundle 120. Accordingly, state-of-the-art electrode assembly 100 may only achieve an activation of a small percentage of the nerve axons in the nerve bundle 120. Some estimates have suggested that as little as 5% of the total population of nerve axons within a nerve bundle may be activated using state-of-the-art electrode assembly 100.

State-of-the-art electrode assembly 100 may only provide adequate stimulation (i.e., may only modulate electrical activity of) individual nerve fibers (axons) that are in close proximity to the outside surface of the nerve trunk. Some patients may not respond to neurostimulation therapy due to the failure of electrical signals delivered to the outer portions of the nerve trunk 120 to penetrate to a sufficient depth within the nerve trunk to recruit nerve axons that are relevant to the patient's condition. This factor may result in a reduced efficacy of the therapy or in some cases a complete failure of the patient to respond to the therapy.

Another problem associated with the state-of-the-art electrode assembly 100 is that, as a result of the attenuation described above, a signal with larger power than otherwise would have been required, is needed to achieve desired efficacy. Physicians may be compelled to increase the dosage, i.e., frequency, power, pulse width, etc., of stimulation signals to achieve desired efficacy. This excessive usage of power may result in reduced battery life because of the portion of the electrical signal that is non-therapeutic or sub-optimal in achieving therapeutic efficacy.

The present invention is directed to overcoming, or at least reducing, the effects of one or more of the problems set forth above.

SUMMARY OF THE INVENTION

In one aspect, an apparatus is provided for employing an electrode for delivering an electrical signal to a target nerve of a tissue of a patient's body, wherein the nerve comprises an outer surface and an inner portion. The electrode includes an inner surface to contact to the outer surface of the target nerve. The electrode also includes a plurality of fiber elements comprising a proximal end and a distal end. The fiber elements are coupled at the proximal end to the inner surface of the electrode.

In another aspect, an apparatus is provided for employing an electrode for delivering an electrical signal to a target nerve of a tissue of a patient's body, wherein the nerve comprises an outer surface and an inner portion. The electrode includes a first surface to electrically couple to the cranial nerve. The electrode also includes a plurality of fibers having a proximal end and a distal end. Each of the fibers is coupled to the first surface at the proximal end. The fibers are conductive and adapted to migrate beneath the outer surface of the cranial nerve to deliver an electrical signal to the inner portion of the cranial nerve.

In yet another aspect of the present invention, an implantable medical device system is provided for delivering an electrical signal to a portion of a target tissue of a patient's body. The tissue comprises an outer surface and an interior portion. The IMD system includes an IMD for generating an electrical signal. The system also includes an electrode that is operatively coupled to the IMD. The electrode is provided for delivering the electrical signal to the target tissue of a patient's body. The electrode includes a first surface to electrically couple to an outer surface of the target tissue. The electrode also includes a plurality of longitudinal elements coupled to the first surface. The plurality of longitudinal elements are adapted to electrically couple to at least one of the outer surface and the interior portion of the target tissue.

BRIEF DESCRIPTION OF THE DRAWINGS

The invention may be understood by reference to the following description taken in conjunction with the accompanying drawings, in which like reference numerals identify like elements, and in which:

FIG. 6 illustrates a stylized depiction of a portion of an electrode in contact with a nerve, along with stylized, cross-sectional view of the nerve in accordance with one illustrative embodiment of the present invention;

FIG. 7 illustrates a stylized depiction of a fibrous material coupled to an electrode, along with a stylized, magnified depiction of the fibrous material, in accordance with one illustrative embodiment of the present invention.

Figure 1:
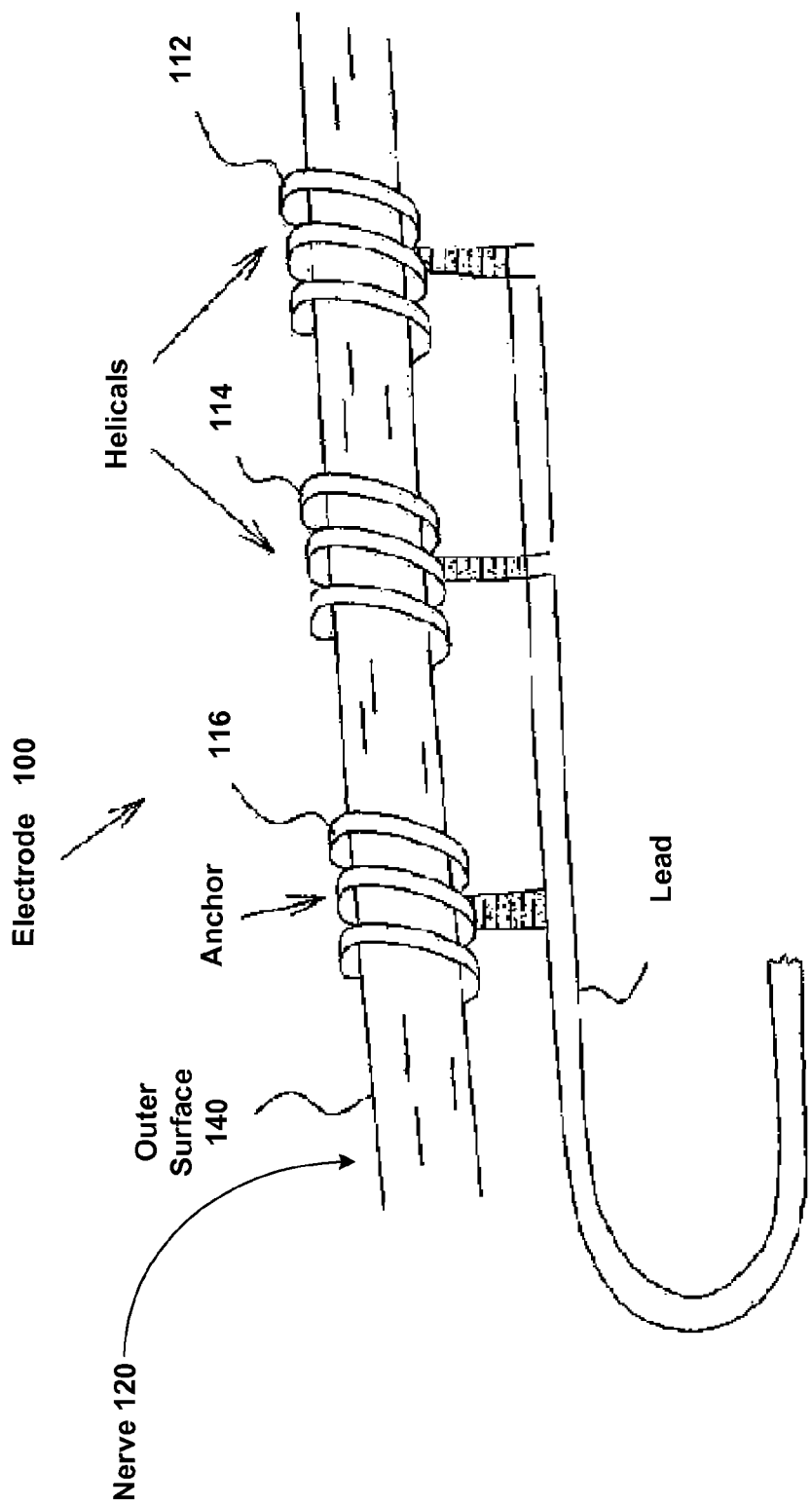
FIG. 1 illustrates a prior art electrode used with implantable medical devices, the electrode being coupled to a nerve trunk.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

Cranial nerve stimulation has been proposed to treat a number of disorders pertaining to or mediated by one or more structures of the nervous system of the body, including epilepsy and other movement disorders, depression, anxiety disorders and other neuropsychiatric disorders, dementia, traumatic brain injury, head trauma, coma, migraine headache, obesity, eating disorders, sleep disorders, cardiac disorders (such as congestive heart failure and atrial fibrillation), hypertension, endocrine disorders (such as diabetes and hypoglycemia) and pain, among others. See, e.g., U.S. Pats. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult or impossible.

Moreover, even if such pathways were known, the precise stimulation parameters that would modulate particular pathways relevant to a particular disorder generally cannot be predicted.

Despite the difficulties of predicting efficacy for particular disorders, the use of vagus nerve stimulation as a therapy for treating epilepsy and/or depression is an established therapy option. Electrodes may be used in a system to deliver therapeutic electrical signals from an IMD to a target portion of a patient's body (e.g., a vagus nerve) for treating these and other diseases. Embodiments of the present invention provide for a "fibrous electrode," which refers to an electrode upon which one or more "fibers" may be coupled. Some embodiments of the present invention provide for a "longitudinal element" coupled to a surface of an electrode. As used herein, a longitudinal element refers to an element whose longest dimension substantially exceeds other dimensions, e.g., length, width, cross-section, etc. Thus, a longitudinal element may comprise a "fiber" as previously disclosed. An example of a fiber may include, but is not limited to, a flexible material that is in mechanical and electrical communication with the electrode. These flexible materials may be formed from carbon nanotubes or interwoven fibers comprising carbon nanotubes, a variety of conductive materials, a variety of semiconductive materials, and/or other materials that are relatively thin, strong and electrically conductive, or combinations of the foregoing. Embodiments of the present invention provide for an electrode that comprises one or more fibers that may be capable of penetrating an outer surface of a target tissue (e.g., a nerve bundle or an individual nerve) upon which the electrode is operatively coupled. Where the target tissue is a nerve bundle, the fibers of the electrode may penetrate the outer surface of a portion of the nerve to reach an interior portion of the nerve bundle to allow an electrical signal to be applied within the nerve bundle. Such an electrode will advantageously allow for greater electrical flux into the target nerve, and may permit recruitment and/or modulation of nerve fibers not capable of modulation with prior art electrodes coupled only to an outer surface of the nerve. Embodiments of the present invention provide for a fibrous neurostimulation electrode that is capable of delivering electrical signals to an interior portion of a cranial nerve.

Utilizing embodiments of the present invention, the penetration of the fibrous material operatively coupled to the electrode into the interior portion of the nerve may be used to cause the electrical signal to penetrate into the interior portions of the tissue to a greater depth than electrodes lacking said fibrous material, e.g., to various nerve fibers (axons) within the nerve bundle. Therefore, utilizing the electrodes of embodiments of the present invention, an increased population of nerve fibers may be modulated by the electrical signal. The "fibrous" or "fiber" electrodes of the present invention provides for conductive communication with an interior portion of the nerve. The fiber or fibrous material may be of one or more of a plurality of materials, such as a stainless steel fiber, a carbon nanotube fiber, a conductive graphite fiber, a titanium fiber, a gold fiber, a copper fiber, silicon oxide, and/or one or more of any of a plurality of conductive materials capable of being formed into fibers of relatively small dimensions, e.g., below 1.0 mm.

The fibrous electrodes disclosed by embodiments of the present invention may also be used for sensing operations. Therefore, the fibers e.g., microfibers or nanofibers, that are coupled to a first electrode may provide for an increased population of nerve fibers being included and observed in sensing operations. Further, utilizing embodiments of the present invention, a decreased amount of current density may be required to modulate a larger number of nerve fibers. This may provide for usage of a lower power stimulation signal, while achieving equal or better delivery of therapeutic signals, and/or may allow therapeutic efficacy to be achieved for patients who otherwise would not respond to the electrical signal therapy.

Embodiments of the present invention provide for applying a predetermined amount of force upon the fibrous electrode, which may prompt the fibers coupled to the electrode to migrate into the nerve bundle in a relatively slow manner. In this manner, penetration of the nerve bundles may be achieved over time without substantially causing excessive trauma to the nerve or surrounding tissue. Further, a multiplexing scheme may be used to deliver current or electrical signals to various portions of a nerve in a predetermined sequence. For example, during a first time period, the electrical signal may be applied to an exterior surface of the nerve using a first surface of the electrode, while during a second time period, the electrical signal may be applied to an interior portion of the nerve using a second, fibrous portion of the electrode. In this manner, a multiplexing scheme may be used to prompt increased diversity of nerve fibers recruited by the electrical signal. Similar benefits may be obtained when the electrode is used to sense electrical activity in the nerve bundle.

Figure 2:
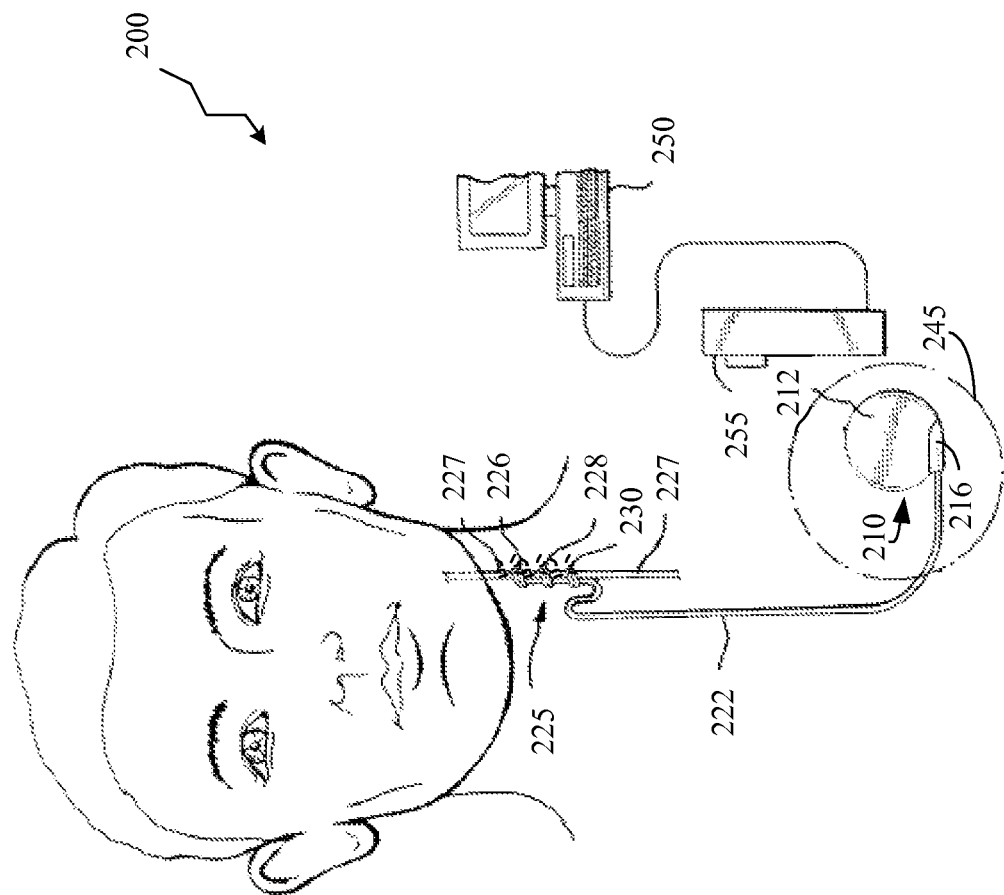
FIG. 2 provides a stylized diagram of a system that includes an IMD and an electrode implanted into a patient's body for providing a therapeutic electrical signal to a neural structure of the patient's body, in accordance with one illustrative embodiment of the present invention.

Although not so limited, a system capable of implementing embodiments of the present invention is described below. FIG. 2 depicts a stylized implantable medical system 200 for implementing one or more embodiments of the present invention. An electrical signal generator 210 is provided, having a main body 212 comprising a case or shell with a header 216 for connecting to an insulated, electrically conductive lead assembly 222. The generator 210 is implanted in the patient's chest in a pocket or cavity formed by the implanting surgeon just below the skin (indicated by a dotted line 245, similar to the implantation procedure for a pacemaker pulse generator.

A fibrous electrode assembly 225, preferably comprising a plurality of electrodes having at least an electrode pair, is conductively connected to the distal end of the lead assembly 222, which preferably comprises a plurality of lead wires (one wire for each electrode). Each electrode in the electrode assembly 225 may operate independently or alternatively, may operate in conjunction with the other electrodes. Each electrode may comprise one or more fibrous electrodes for applying electrical signals to a nerve bundle. In some embodiments, the fibrous portions of the electrode penetrate an outer surface of the nerve bundle to deliver electrical charge to an interior of the nerve bundle. In other embodiments, the fibers do not penetrate into the interior of the nerve, but provide for a higher charge flux into the target portion of the nerve compared to prior art electrodes. Some prior art electrodes for stimulation of neural tissues have extremely small surface areas, resulting in relatively high electrical flux across that area. When the electrical flux exceeds a threshold, the molecules of the metal electrode can be dissolved into the surrounding body fluids, which is usually toxic to the neural tissue. Because the fibers coupled to the electrode significantly increase the surface area across which the electrical charge is transferred, it provides a significantly reduced risk of electrode dissolution, thereby providing increased safety where a patient is treated with relatively strong electrical signals.

Referring again to FIG. 2, lead assembly 222 is attached at its proximal end to connectors on the header 216 of generator 210. The electrode assembly 225 may be surgically coupled to a vagus nerve 227 in the patient's neck or at another location, e.g., near the patient's diaphragm or at the esophagus/stomach junction. Other (or additional) cranial nerves, such as the trigeminal and/or glossalpharangeal nerves may also be used to deliver the electrical signal in particular alternative embodiments. In one embodiment, the electrode assembly 225 comprises a bipolar stimulating electrode pair 226, 228. Suitable electrode assemblies which could be modified to provide embodiments of the present invention are available from Cyberonics, Inc., Houston, Tex., USA as the Model 302 electrode assembly. However, persons of skill in the art will appreciate that many prior art electrode designs could be modified to provide embodiments of the present invention. Moreover, other electrodes, such as spinal cord electrodes, deep brain stimulation (DBS) electrodes, electrodes for muscle stimulation, and electrodes for stimulation of organs or even bones could also be modified to provide embodiments of the present invention. In one embodiment, the two electrodes are wrapped about the vagus nerve, and the electrode assembly 225 may be secured to the nerve 227 by a spiral anchoring tether 230, such as that disclosed in U.S. Pat. No. 4,979,511 issued Dec. 25, 2990 to Reese S. Terry, Jr., and assigned to the same assignee as the instant application. Lead assembly 222 is secured, while retaining the ability to flex with movement of the chest and neck, by a suture connection to nearby tissue (not shown). While the electrode assembly 225 in FIG. 2 is described in terms of a stimulating electrode, it will be appreciated that in alternative embodiments, the electrode assembly 225 may comprise a sensing electrode for sensing, e.g., heart rate, electrical activity in the target nerve, temperature, or other body parameters.

The electrical pulse generator 210 may be programmed with an external device, such as computer 250 using programming software known in the art of implantable medical devices. A programming wand 255 may be coupled to the computer 250 as part of the external device to facilitate radio frequency (RF) communication between the computer 250 and the pulse generator 210. The programming wand 255 and computer 250 permit non-invasive communication with the generator 210 after the latter is implanted. In systems where the computer 250 uses one or more channels in the Medical Implant Communications Service (MICS) bandwidths, the programming wand 255 may be omitted to permit more convenient communication directly between the computer 250 and the pulse generator 210.

Figure 3:
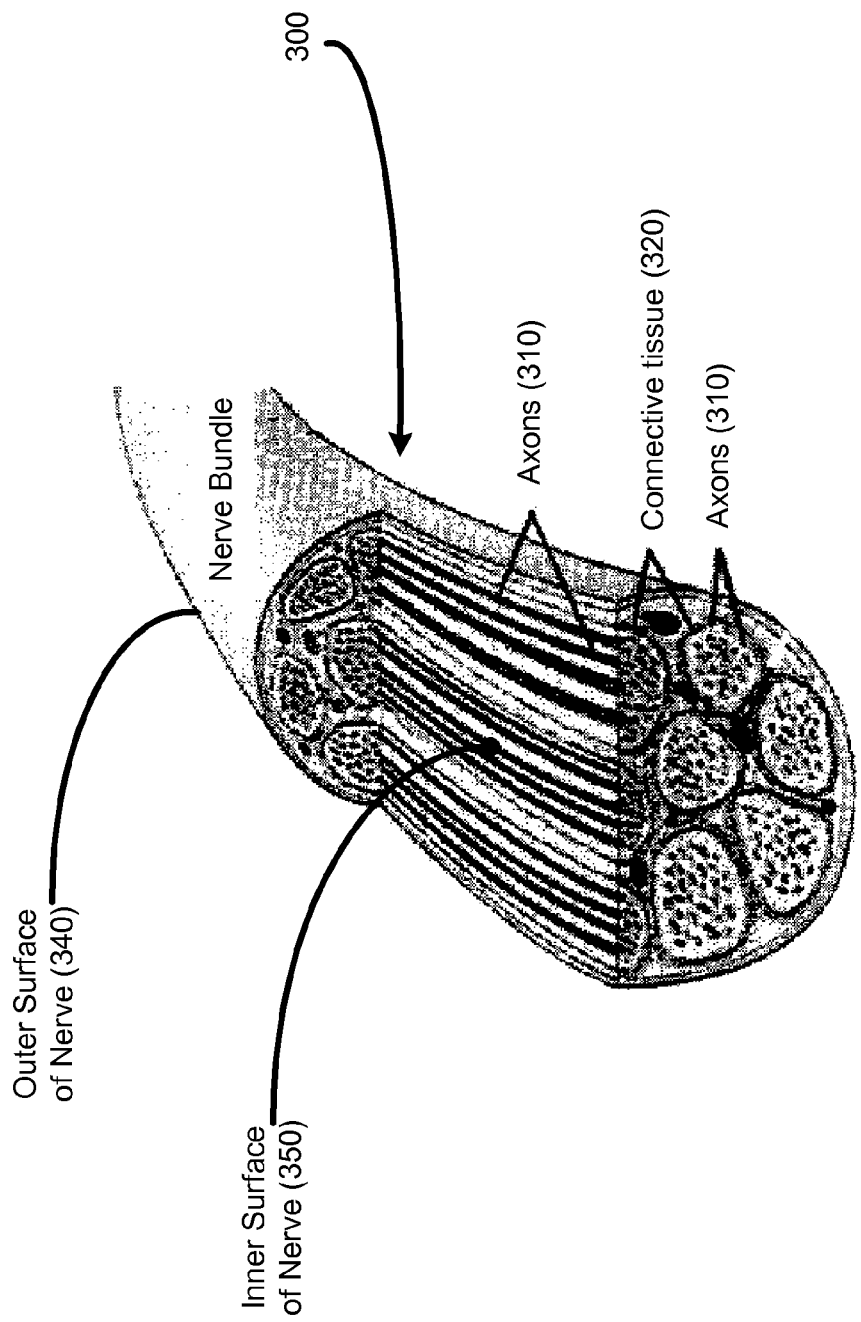
FIG. 3 illustrates a stylized depiction of a cross-sectional depiction of a target nerve for a therapeutic electrical signal.

Turning now to FIG. 3, a cross-sectional stylized view of a nerve or a nerve bundle 300 is illustrated. The nerve or nerve bundle 300 may comprise an outer surface 340 and an inner portion 350 comprising a plurality of axons 310 and connective tissue 320. The axons 310 transport electrical action potentials along the axis of the nerve 300. Typically, one or more axons 310 affecting the patient's medical condition may not be sufficiently stimulated using state-of-the-art electrodes that deliver electrical signals to the exterior surface of the nerve bundle 300. Embodiments of the present invention provide for more robust stimulation since internal portions of the nerve may be more directly stimulated, and/or lower electrical flux values across the electrode providing increased safety.

Figure 4:
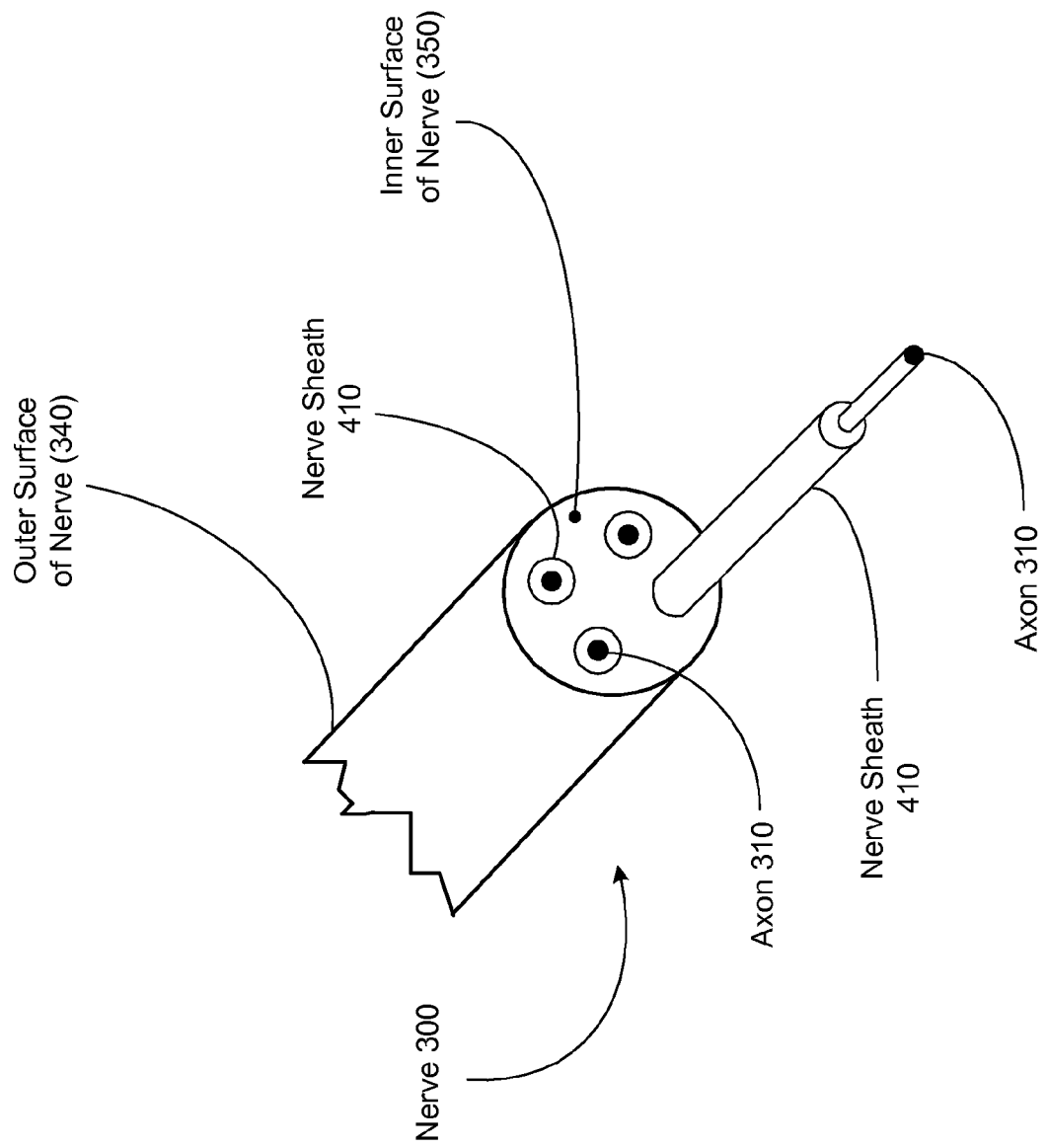
FIG. 4 illustrates a cross-sectional view of a nerve, including a stylized isometric depiction of mylinated axon and an unmyelinated axon.

Referring to FIG. 4, a cross-sectional view of the nerve bundle 300 with a stylized, isometric depiction of a myelin nerve sheath 410 surrounding an axon 310 is illustrated. It is known in the art that large nerve bundles, such as the vagus nerve, include multiple nerve types nerves, such as A and B fibers, which are large-diameter fibers having a myelin sheath such as sheath 410, and C fibers, which are small-diameter fibers lacking a myelin coating. These major fiber types also have numerous sub-types. The A and B fibers typically conduct action potentials at much faster speeds along the nerve than C fibers, and have a lower threshold for the induction of action potentials with an applied electric signal. Typically, the electric signal applied to the exterior of the nerve bundle 300 may at least partially attenuate as it travels radially from the outer surface 340 of the nerve 300 to interior portion 350 and towards the central axis. Accordingly, axons of a given type near the outer surface 340 are more likely to receive sufficient electrical charge to induce an action potential than are axons in the interior portion of the nerve 300, with the likelihood of a given electrical charge inducing an action potential in an individual axon decreasing radially from the outer surface 340 to the central axis of the nerve. Embodiments of the present invention provide for fibrous electrodes that may penetrate the surface of the nerve 300 and/or the nerve sheath 410 to enhance delivery of electrical charge to axons near the center of the nerve 300. In this manner, a greater percentage of various nerve fibers within the nerve bundle 300, such as the A fibers, the B fibers and/or the C fibers may be targeted and stimulated sufficiently to induce action potentials, as compared to prior art electrodes.

Figure 5A:
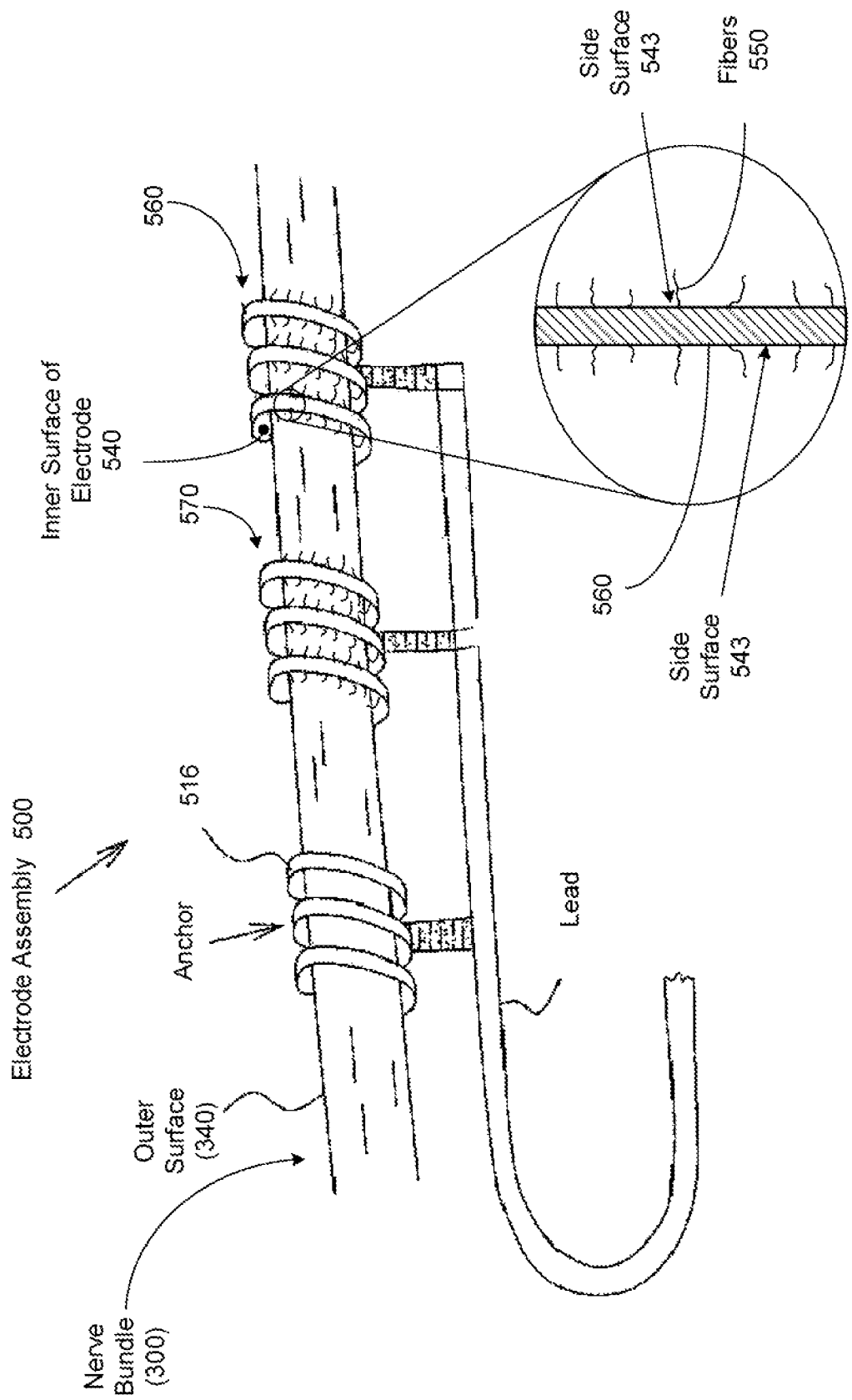
FIG. 5A illustrates an electrode coupled to a nerve, in accordance with one illustrative embodiment of the present invention.
Figure 5B:
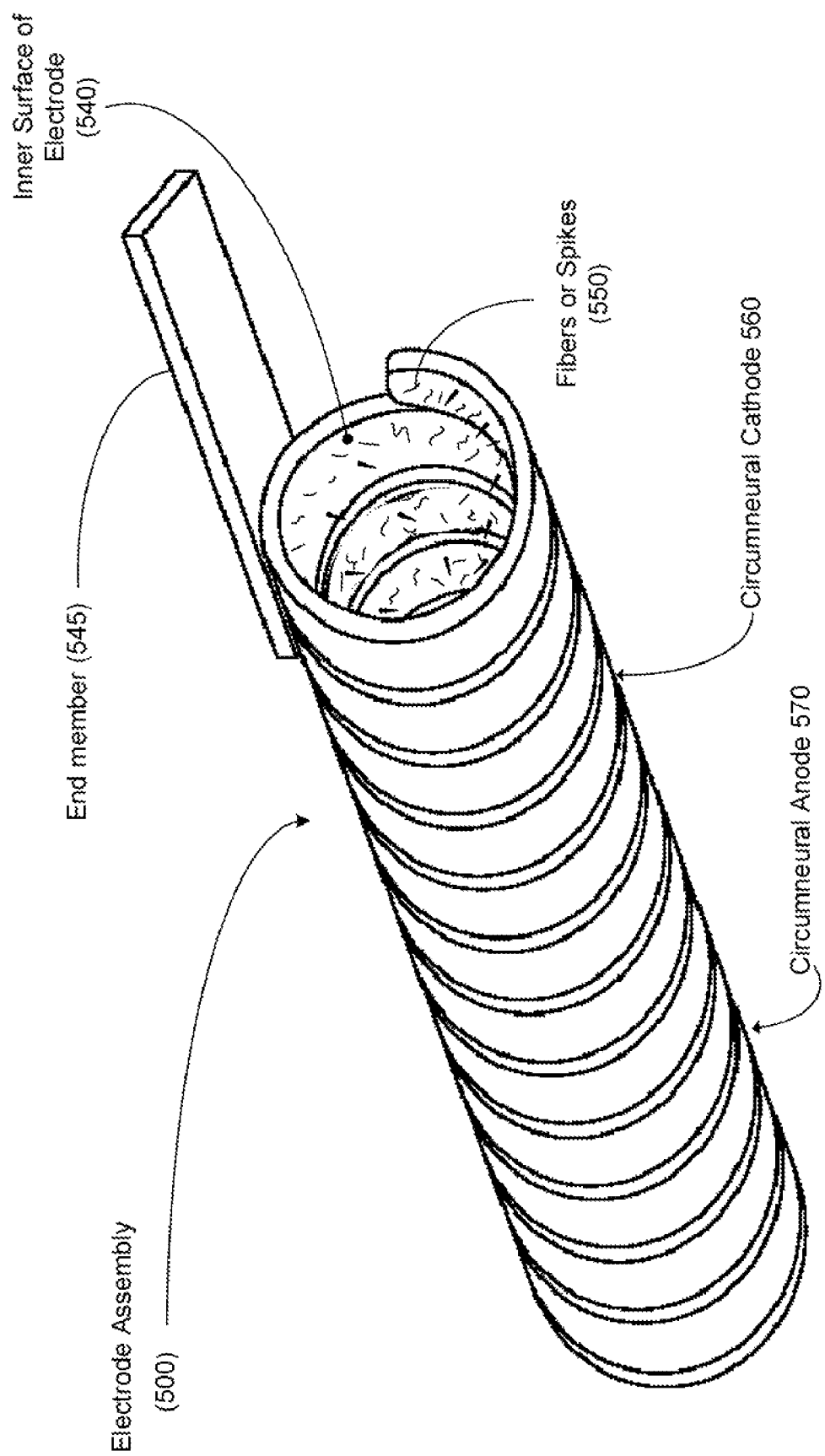
FIG. 5B illustrates a helical configuration of the electrode, in accordance with one illustrative embodiment of the present invention.

Referring simultaneously to FIGS. 5A and 5B, an electrode assembly comprising fibers and/or spikes on its inner surface, capable of being engaged to a tissue (e.g., a nerve bundle 300) of a human body, is provided. FIG. 5A illustrates an electrode assembly 500 in contact with a nerve bundle 300, in accordance with one illustrative embodiment of the present invention. FIG. 5B illustrates a helical electrode, wherein an inner surface 540 of a circumneural cathode 560 or a circumneural anode 570 comprises a plurality of fibers and/or spikes 550 coupled thereto. Nerve bundle 300 is generally cylindrical and comprises a central axis. The electrode assembly 500 of FIG. 5A may comprise a plurality of fiber elements 550 that are coupled to the circumneural cathode 560 or the circumneural anode 570. The fibers 550 may refer to a plurality of materials that are conductive and suitable for joining to an inner surface 540 of the circumneural cathode 560 or the circumneural anode 570. Inner surface 540 is suitable for engaging outer surface 340 of the nerve bundle 300, while fibers 550 may engage either outer surface 340 or an inner portion 350 of the nerve bundle 300. The fibers 550 may deliver the electrical signals directly to any portion of the nerve 300 with which in comes into contact. In one embodiment, the electrode assembly 500 is a helical shaped apparatus (as depicted in FIG. 5B) that may be wrapped about the nerve bundle 300. FIG. 5B also illustrates an end member 545 that provides an interface to a lead wire in electrical communication with the IMD. In one embodiment, the electrode assembly 500 comprises at least a first circumneural cathode portion 560 and a second circumneural anode portion 570. The first circumneural portion 560 and/or the second circumneural portion 570 comprise a plurality of fibers 550 described herein for contacting a portion of the target nerve bundle 300.

FIG. 5A also illustrates a stylized magnification of a portion of the electrode assembly 500. In the circumneural electrode assembly 500, each element 560, 570 may comprise a number of fibers 550 that protrude outward from the inner surface 540 of the element 560, 570 and/or from the side surfaces 543 of the element 560, 570 at one or more angles relative to the inner surface 540 or the side surfaces 543. In one embodiment, the fibers 550 in the inner surface 540 of the electrode may protrude radially inwardly from the inner surface 540 of the elements 560, 570 toward the axis of the nerve bundle 300 (as exemplified in FIGS. 5A and 5B). The fibers 550 may be coupled to the element 560, 570 in a number of ways, including soldering, micro-welding, using adhesives, photolithography process, and/or various manufacturing techniques, etc. The fibers 550 may be of a flexible configuration, a medium rigid configuration, and/or of a rigid configuration (e.g., a spike). They may also be, in some embodiments, of non-uniform cross-section, e.g., thicker at the proximal end and narrowing at the distal end. The fiber 550 may be a longitudinal element, which may refer to an element whose longest dimension substantially exceeds other dimensions, e.g., length, width, cross-section, etc. Thus, a longitudinal element may comprise a "fiber" as previously disclosed.

The fibers 550 provide for an electrical path from the IMD 200, through the lead assembly 222, through the element 560, 570, and onto an inner portion of a nerve bundle 300. More specifically, the electrode assembly 500 provides a path from the fibers 550 and inner surface 540 of the cathode element 560, through the outer surface 340 of the nerve and into the inner portion 350 thereof, through the nerve tissue and into the fibers 550 and inner surface 540 of the anode element 570.

Turning now to FIG. 6, a stylized depiction is provided of a portion of an element (560, 570) of the electrode assembly 500 in contact with a nerve bundle 300. FIG. 6 also depicts a stylized, cross-sectional view of the nerve bundle 300, in accordance with one embodiment of the present invention. The element 560, 570 may comprise an inner surface 540 and number of fibers 550. For clarity of illustration inner surface 540 is shown in only partial contact with outer surface 340 of nerve 300. However, in an actual embodiment, substantially all of inner surface 540 would engage outer surface 340 of nerve 300. The fibers 550 may engage either outer surface 340 or inner portion 350 of nerve 300. The fibers may penetrate, through migration, the surface of the nerve 300 over a period of time (e.g., many days, weeks, etc.). In one embodiment, external force may be applied to prompt the migration of the fibers 550 into the nerve bundle 300. In an alternative embodiment, the electrode assembly 500 may be positioned around the nerve 300 in a manner, such that without applying external force, the fibers 550 may penetrate the surface of the nerve bundle 300. In one such embodiment, electrode elements 560, 570 may comprise a resilient material, such as a silicone polymer or other known biocompatible materials. The electrode elements may be formed to provide a slight constrictive resilient force on nerve 300 to maintain contact between the electrode element (560, 570) and the nerve 300, and to assist fibers 550 to penetrate into the inner portion 350 of nerve bundle 300.

In one embodiment, the penetration of the fibers 550 into the nerve 300 may take place at such a rate that trauma to the nerve 300 is eliminated. In yet another alternative embodiment, migration of the fibers 550 may be controlled by electrical means (e.g., by providing predetermined electrical pulses to prompt migration of the fibers 550) such that the fibers 550 may penetrate the outer surface 340 of the nerve 300 substantially without causing excessive damage to the nerve. Other means, such as external force, small movement, etc., may be used to cause the penetration of the fibers into the neurons. In still another embodiment, fibers 550 may be formed of a shape-memory metal such as Nitinol, and coupled by known means substantially perpendicular to inner surfaces 540 of an electrode element. The fibers may then be substantially flattened against inner surface 540 by mechanical means, thereby rendering the electrode element easier and safer to couple to the nerve. The shape-memory metal may be fabricated to return to its fabrication state (i.e., substantially perpendicular to inner surface 540) at a predetermined temperature, e.g., a temperature at or slightly above or below body temperature. Thus, after the electrode assembly 500 is wrapped around the nerve 300, the temperature of the patient's body causes the fibers 550 to return to a substantially perpendicular orientation relative to inner surface 540 to facilitate penetration of the fibers 550 into inner portion 350 of the nerve 300.

FIG. 6 further illustrates that, in some cases, some fibers 550 of the electrode assembly 500 may penetrate various portions of the nerve bundle 300. By providing fibers of differing lengths, nerve fibers at various radial distances from the outer surface 340 may be selectively targeted for stimulation.

FIG. 7 illustrates a stylized, magnified depiction of one embodiment of a fiber 550 of a circumneural cathode 560 or a circumneural anode 570, in accordance with one illustrative embodiment of the present invention. In some embodiments of the present invention, the fiber 550 may comprise a fiber insulation 710 and a conductive portion 720. A segment of the conductive portion 720 may be encapsulated by a fiber insulation 710 such that only the exposed portion of the fiber 550 (i.e., the conductive portion 720) is capable of delivering a stimulation signal. In this manner, penetration to particular radial depths within the nerve 300 may be achieved. For example, referring simultaneously to FIGS. 6 and 7, a fiber 550 that penetrates the surface of the nerve bundle 300 and moves into significant proximity of the axons 310 may have an exposed conductive portion 720 that comes into contact with the axons 310. In other words, the remaining portion of the fiber 550 (i.e., the portion from the inner surface 540 of the electrode through the nerve bundle 300, and to a desired depth within interior portion 350 of the nerve bundle) is insulated and only the tip of the nerve of the fiber 550 is exposed. Thus, only the axons 310 in the immediate vicinity of the conduction portion 720 of the fiber 550 will be stimulated. Therefore, a specific targeting and/or more effective stimulation, of A-fibers, B-fibers, C-fibers and/or the axons 310 in the interior portion 350 of the nerve 300 may be achieved by insulating portions of the fiber 550 and exposing only the conductive portion 720 to target more specific regions of the nerve bundle 300.

In alternative embodiments substantially the entire length of the fibers 550 may be conductive, and penetration of charge into specific areas of the inner portion 350 of the nerve 300 may be controlled by the distribution and length of the fibers 550.

Figure 8:
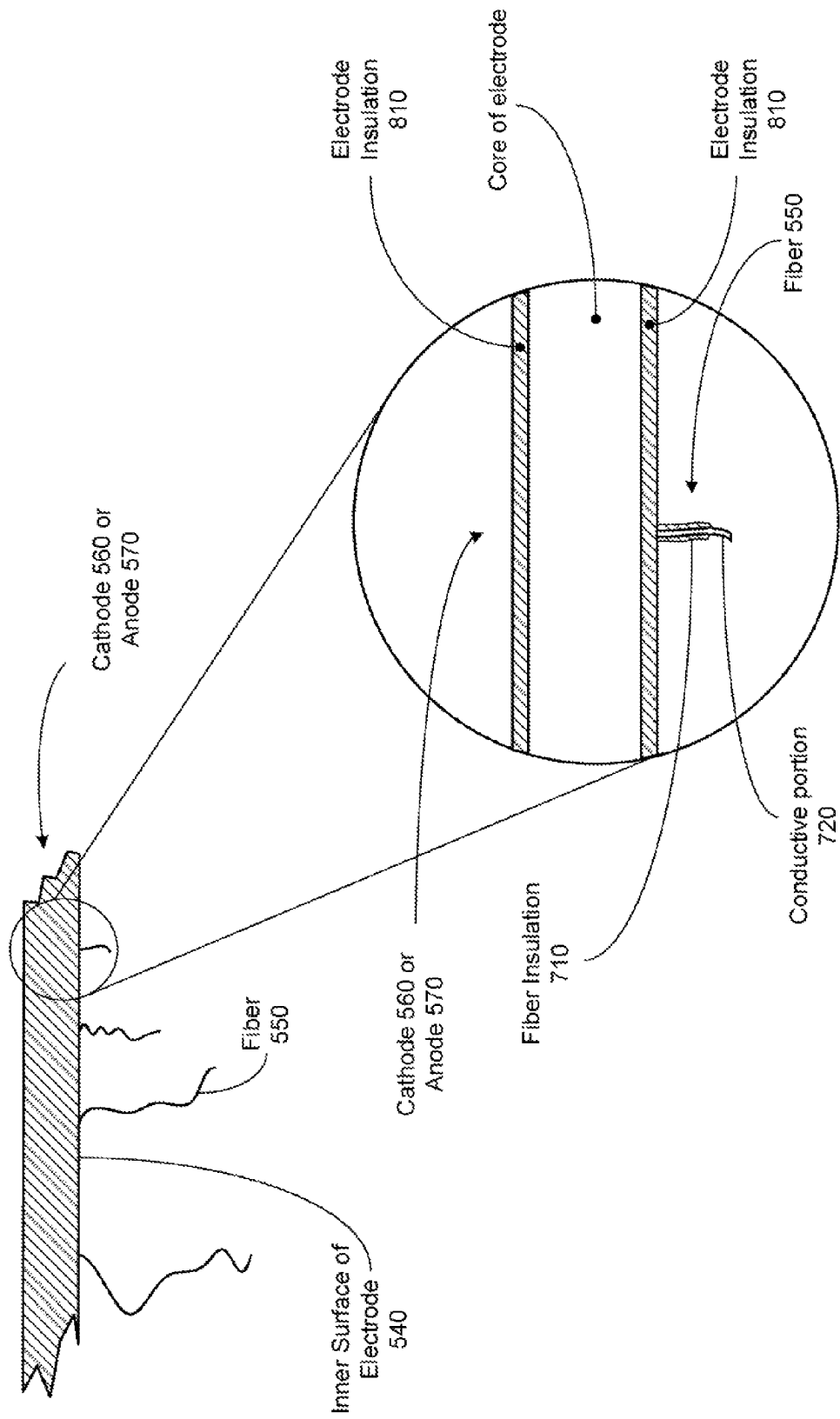
FIG. 8 illustrates a stylized, magnified, cross-sectional depiction of an electrode with an insulating material, in accordance with one illustrative embodiment of the present invention.

FIG. 8, illustrates a stylized, magnified, cross-sectional depiction of a portion of the circumneural cathode 560 or the circumneural anode 570 and associated fibers 550, in accordance with an illustrative embodiment of the present invention. In this embodiment of the present invention, the inner surface 540 of circumneural cathode 560 or circumneural anode 570 may be coated with an insulating material (electrode insulation 810), similar to the insulation 710 on portions of the fibers 550, discussed above with respect to FIG. 7. In this configuration, neither the inner surface 540 of circumneural cathode 560 or circumneural anode 570 nor the insulated portions of the fiber 550 provide electrical stimulation to the nerve. Instead, only the conductive portion 720 (i.e., the exposed tip) of the fiber 550 delivers the electrical signal to the nerve 330. Therefore, a more focused delivery of the stimulation signal may be provided to the interior 350 of the nerve 300, as opposed to the exterior 340. Thus, portions of the nerve bundle 300 may be specifically targeted without providing stimulation to other portions of a nerve bundle 300. In this manner, focused delivery of stimulation to specific portions of a nerve bundle 300 may be achieved. Utilizing multiplexing of delivery of the electrical signal, a sequence of targeted electrical signals throughout a nerve bundle 300 may be achieved for increased efficacy and targeted delivery of stimulation signals.

Utilizing embodiments of the present invention, a more robust delivery of electrical signal/stimulation may be achieved. This may increase efficacy and provide various advantages, such as increased population of nerve fibers being activated by stimulation. Further advantages provided by embodiments of the present invention may include increased population of nerve fibers being accessed for observation during sensing operations. These advantages may lead to a reduction of the power used by the IMD since more direct current electrical signals may be provided.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the methods described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy. More generally, the techniques and apparatus of the present invention may be applied to any neural structure with regard to which a more controlled delivery of an electrical signal throughout the structure (as opposed to its periphery only) is desired or needed.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. An electrode assembly for delivering an electrical signal to a target nerve or nerve bundle of a patient's body, wherein said nerve or nerve bundle comprises an outer surface and an inner portion, said electrode comprising:
   a circumneural cathode adapted to substantially surround a first longitudinal portion of said target nerve or nerve bundle, said circumneural cathode comprising an inner surface adapted to contact said outer surface of said target nerve or nerve bundle, and a first plurality of fiber elements comprising a proximal end and a distal end, wherein said fiber elements are coupled at said proximal end to said inner surface of said circumneural cathode and said fiber elements are capable of migrating into said inner portion of said target nerve or nerve bundle; and
   a circumneural anode adapted to substantially surround a second longitudinal portion of said target nerve or nerve bundle, said circumneural anode comprising an inner surface adapted to contact said outer surface of said target nerve or nerve bundle, and a second plurality of fiber elements comprising a proximal end and a distal end, wherein said fiber elements are coupled at said proximal end to said inner surface of said circumneural anode and said fiber elements are capable of migrating into said inner portion of said target nerve or nerve bundle.

2. The electrode assembly of claim 1, wherein said plurality of fiber elements are adapted to migrate into said inner portion of said target nerve or nerve bundle.

3. The electrode assembly of claim 1, wherein said fiber elements are comprised of at least one conductive material selected from the group consisting of copper, titanium, an alloy metal, iron, steel, and a carbon-based structure.

4. The electrode assembly of claim 3, wherein each of said fiber elements comprises an electrically insulated portion proximate to said proximal end and a conductive portion proximal to said distal end.

5. The electrode assembly of claim 1, wherein said target nerve or nerve bundle is a cranial nerve selected from the group consisting of a vagus nerve, a glossopharyngeal nerve, and a trigeminal nerve, and said fiber elements are capable of penetrating said outer surface of said target nerve or nerve bundle.

6. The electrode assembly of claim 1, wherein said fiber elements comprise a variety of lengths adapted to penetrate a plurality of distances into said target nerve or nerve bundle.

7. The electrode assembly of claim 6, wherein said inner surface of said electrode is substantially nonconductive, and wherein a first portion of said fiber elements is encapsulated with an electrically insulating material, electrically exposing a conductive second portion of said fiber element to said target nerve or nerve bundle.

8. The electrode assembly of claim 1, wherein said electrode further comprises an electrical signal to apply to said target nerve or nerve bundle to treat at least one of depression disorder and an epilepsy disorder.

9. The electrode assembly of claim 1, wherein said electrode is operative to sense an electrical activity in said target nerve or nerve bundle.

10. The electrode assembly of claim 1, wherein said distal ends of said plurality of fiber elements migrate into said inner portions of said target nerve or nerve bundle in response to one or more electrical pulses provided to the electrode.

11. The electrode assembly of claim 1, wherein said circumneural cathode, said circumneural anode, or both is further adapted to apply an electrical signal to said outer surface of said target nerve or nerve bundle.

12. An electrode assembly for delivering an electrical signal to a portion of a cranial nerve of a patient's body, said cranial nerve having an outer surface and an inner portion, said electrode assembly comprising:
   a circumneural cathode adapted to substantially surround a first longitudinal portion of said cranial nerve; and
   a circumneural anode adapted to substantially surround a second longitudinal portion of said cranial nerve;
   wherein said circumneural cathode and circumneural anode each comprise:
   a first surface adapted to electrically couple to said cranial nerve; and
   a plurality of fibers having a proximal end and a distal end, wherein each of said fibers is coupled to said first surface at said proximal end, said fibers being conductive and adapted to penetrate beneath the outer surface of the cranial nerve to deliver an electrical signal to said inner portion of said cranial nerve, wherein said plurality of fibers are comprised of a carbon nanotube structure.

13. The electrode assembly of claim 12, wherein said first surface is a helical structure adapted to be wrapped around said cranial nerve.

14. The electrode assembly of claim 12, wherein said fibers are oriented generally perpendicular to said first surface of said electrode.

15. The electrode assembly of claim 12, wherein said plurality of fibers are comprised of a shape-memory metal capable of returning to a desired orientation upon reaching a threshold temperature.

16. An implantable medical device system for providing an electrical signal therapy to a patient, comprising:
an implantable medical device for generating an electrical signal; and
an electrode assembly operatively coupled to said implantable medical device for delivering said electrical signal to a portion of a target tissue of a patient's body, said target tissue comprising an outer surface and an interior portion, said electrode assembly comprising:
a circumneural cathode adapted to substantially surround a first longitudinal portion of said target tissue; and
a circumneural anode adapted to substantially surround a second longitudinal portion of said target tissue;
wherein said circumneural cathode and circumneural anode each comprise:
a first surface adapted to electrically couple to said outer surface of said target tissue; and
a plurality of fibers coupled to said first surface, said fibers being capable of migrating within said interior portion of said target tissue.

17. The implantable medical device system of claim 16, further comprising a lead assembly, said lead assembly comprising a proximal portion adapted to be connected to the implantable medical device and a distal portion being adapted to be coupled to said electrode, said lead assembly to carry said electrical signal from said implantable medical device to said electrode assembly.

18. The implantable medical device system of claim 16, wherein said fiber elements are comprised of at least one conductive material selected from the group consisting of copper, titanium, an alloy metal, iron, steel, a shape memory metal, and a carbon-based structure.

* * * * *